(12) United States Patent
Wakabayashi (10) Patent No.: US 9,642,599 B2
(45) Date of Patent: May 9, 2017

(54) ULTRASOUND TRANSDUCER AND ULTRASOUND TRANSDUCER MANUFACTURING METHOD

(71) Applicant: OLYMPUS CORPORATION, Tokyo (JP)

(72) Inventor: Katsuhiro Wakabayashi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/716,192

(22) Filed: May 19, 2015

(65) Prior Publication Data

US 2015/0245815 A1   Sep. 3, 2015

Related U.S. Application Data

(63) Continuation of application No. PCT/JP2014/063211, filed on May 19, 2014.

(30) Foreign Application Priority Data

Jul. 26, 2013   (JP) .................................. 2013-155817

(51) Int. Cl.
*H01L 41/29* (2013.01)
*C25D 3/12* (2006.01)
(Continued)

(52) U.S. Cl.
CPC .......... *A61B 8/4494* (2013.01); *A61B 8/4444* (2013.01); *B06B 1/0633* (2013.01);
(Continued)

(58) Field of Classification Search
CPC ... A61B 8/4494; A61B 8/4444; A61B 8/4483; H01L 41/29; H01L 41/0475;
(Continued)

(56) References Cited

U.S. PATENT DOCUMENTS 4,437,943 A    3/1984  Beck et al.
6,863,209 B2 *  3/2005  Rinne .................. B23K 1/0004
                                                   219/129

(Continued)

FOREIGN PATENT DOCUMENTS

EP    1769854 A1    4/2007
EP    1808131 A1    7/2007
(Continued)

OTHER PUBLICATIONS

Extended Supplementary European Search Report dated Jun. 9, 2016 in related European Application No. 14 82 9955.5.
(Continued)

*Primary Examiner* — Daniel L Murphy
(74) *Attorney, Agent, or Firm* — Scully, Scott, Murphy & Presser, P.C.

(57) ABSTRACT

An ultrasound transducer according to the invention includes: a piezoelectric element; an electrode formed on a surface of the piezoelectric element; a conductive wire including a distal end that is in contact with the electrode; and a metal film formed by an electroplating method, the metal film coating at least the distal end of the wire and the electrode that are in contact with each other and thereby electrically connecting the electrode and the wire.

11 Claims, 10 Drawing Sheets

(51) Int. Cl.
  *A61B 8/00* (2006.01)
  *H01L 41/047* (2006.01)
  *C25D 7/06* (2006.01)
  *G10K 11/26* (2006.01)
  *H01L 41/08* (2006.01)
  *H01L 41/187* (2006.01)
  *G01N 29/24* (2006.01)
  *B06B 1/06* (2006.01)

(52) U.S. Cl.
  CPC ............ *C25D 3/12* (2013.01); *C25D 7/0607* (2013.01); *G01N 29/2437* (2013.01); *G10K 11/26* (2013.01); *H01L 41/0475* (2013.01); *H01L 41/0825* (2013.01); *H01L 41/1876* (2013.01); *H01L 41/29* (2013.01); *A61B 8/4483* (2013.01)

(58) Field of Classification Search
  CPC ............ H01L 41/0825; H01L 41/1876; B06B 1/0633; C25D 7/0607; C25D 3/12; G10K 11/26; G01N 29/2437
  USPC ........................................................ 367/140
  See application file for complete search history.

(56) References Cited

U.S. PATENT DOCUMENTS

| | | | | |
|---|---|---|---|---|
| 7,531,946 | B2 * | 5/2009 | Yamauchi | G10K 9/122 310/324 |
| 2001/0020545 | A1 | 9/2001 | Eldridge et al. | |
| 2002/0156373 | A1 | 10/2002 | Wakabayashi et al. | |
| 2006/0022558 | A1 | 2/2006 | Bindig et al. | |
| 2007/0216257 | A1 | 9/2007 | Fujimura et al. | |
| 2008/0084137 | A1 | 4/2008 | Wakabayashi et al. | |

FOREIGN PATENT DOCUMENTS

| | | |
|---|---|---|
| EP | 1993321 A1 | 11/2008 |
| JP | 2002-095090 A | 3/2002 |
| JP | 2002-186619 A | 7/2002 |
| JP | 2002-224104 A | 8/2002 |
| JP | 2004-349466 A | 12/2004 |
| JP | 2005-533386 A | 11/2005 |
| JP | 2006-110139 A | 4/2006 |
| JP | 2006-320512 A | 11/2006 |
| JP | 2007-243640 A | 9/2007 |
| JP | 2012-034159 A | 2/2012 |
| WO | WO 2004/010511 A2 | 1/2004 |
| WO | WO 2006/009220 A1 | 1/2006 |
| WO | WO 2006/040972 A1 | 4/2006 |
| WO | WO 2007/102424 A1 | 9/2007 |
| WO | WO 2010/035714 A1 | 4/2010 |

OTHER PUBLICATIONS

International Search Report dated Jul. 29, 2014 issued in PCT/JP2014/063211.

Japanese Office Action dated Nov. 18, 2014 issued in JP 2014-548228.

* cited by examiner

ULTRASOUND TRANSDUCER AND ULTRASOUND TRANSDUCER MANUFACTURING METHOD

CROSS REFERENCE TO RELATED APPLICATION

This application is a continuation application of PCT/JP2014/063211 filed on May 19, 2014 and claims benefit of Japanese Application No. 2013-155817 filed in Japan on Jul. 26, 2013, the entire contents of which are incorporated herein by this reference.

BACKGROUND OF THE INVENTION

1. Field of the Invention

The present invention relates to an ultrasound transducer including piezoelectric elements, and an ultrasound transducer manufacturing method.

2. Description of the Related Art

In the field of medical image diagnosis in which an inner structure of a living body is observed and the field of non-destructive tests in which the inside of, e.g., a mechanical structure is observed, ultrasound observation apparatuses that use ultrasound emitted from an ultrasound observation section including piezoelectric elements are used. For example, Japanese Patent Application Laid-Open Publication No. 2002-224104 discloses an ultrasound observation section including a piezoelectric element array formed by arrangement of a plurality of piezoelectric elements. In the ultrasound observation section including the piezoelectric element array, a direction of transmission of an ultrasound beam can electronically be changed.

SUMMARY OF THE INVENTION

An ultrasound transducer according to an aspect of the present invention includes: a piezoelectric element; an electrode formed on a surface of the piezoelectric element; a conductive wire including a distal end that is in contact with the electrode; and a metal film formed by an electroplating method, the metal film coating at least the distal end of the wire and the electrode that are in contact with each other and thereby electrically connecting the electrode and the wire.

Also, an ultrasound transducer manufacturing method according to an aspect of the present invention includes: a first step of bringing a distal end of a conductive wire into contact with an electrode formed on a surface of a piezoelectric element; and a second step of, with the distal end of the wire and the electrode in contact with each other, coating at least the distal end of the wire with a metal film formed by an electroplating method and further coating the electrode, and thereby electrically connecting the wire and the electrode.

DETAILED DESCRIPTION OF THE PREFERRED EMBODIMENTS

A preferred embodiment of the present invention will be described below with reference to the drawings. Note that in each of the drawings used for the below description, components are illustrated on difference scales so that the respective components have sizes that are large enough to be recognized in the drawing, and the present invention is not limited only to the counts and amounts, and the shapes of the components, and the size ratios and the relative positional relationships among the components illustrated in the drawings.

Figure 1:
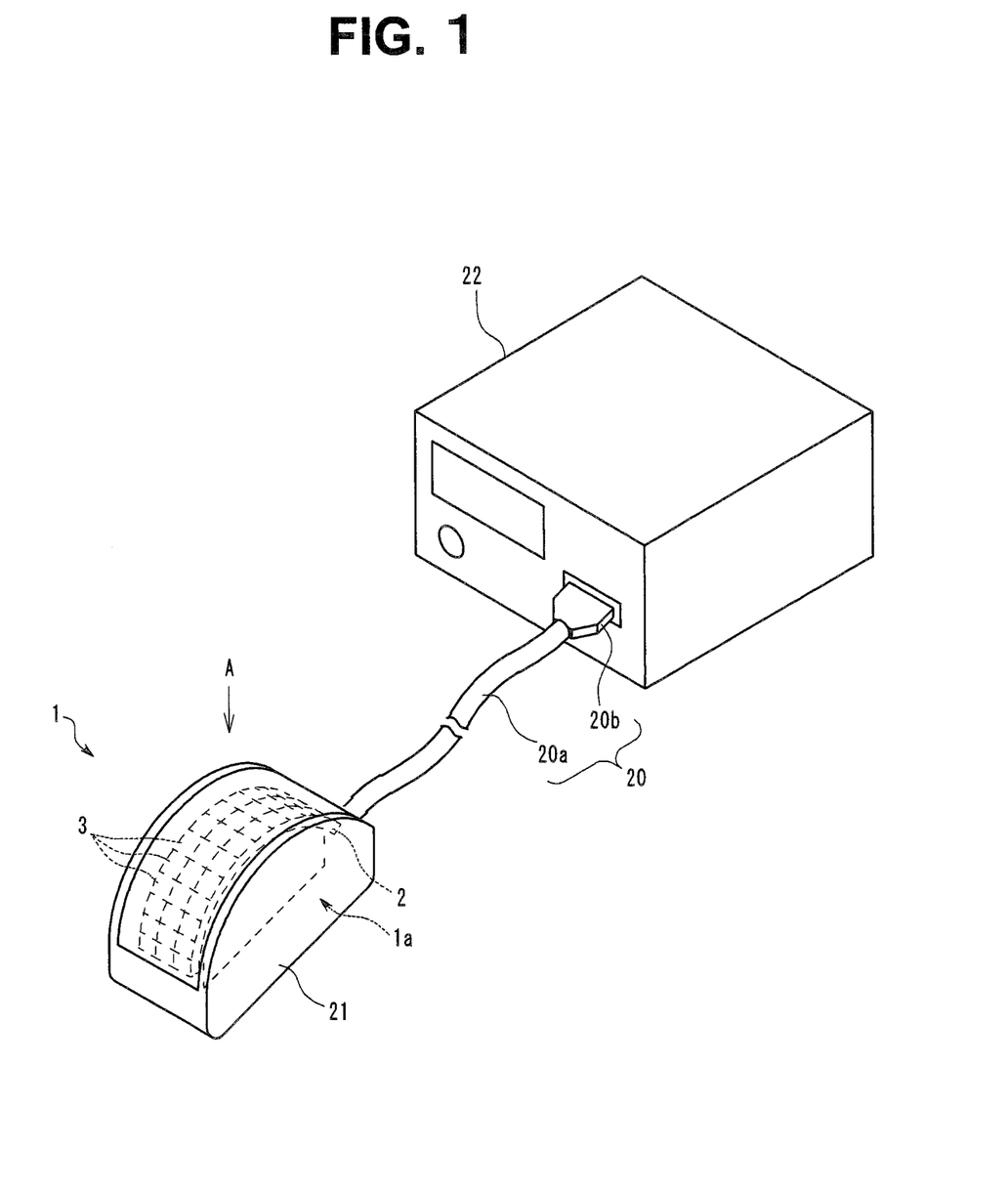
FIG. 1 is a perspective view of an ultrasound transducer connected to an ultrasound observation apparatus.
Figure 2:
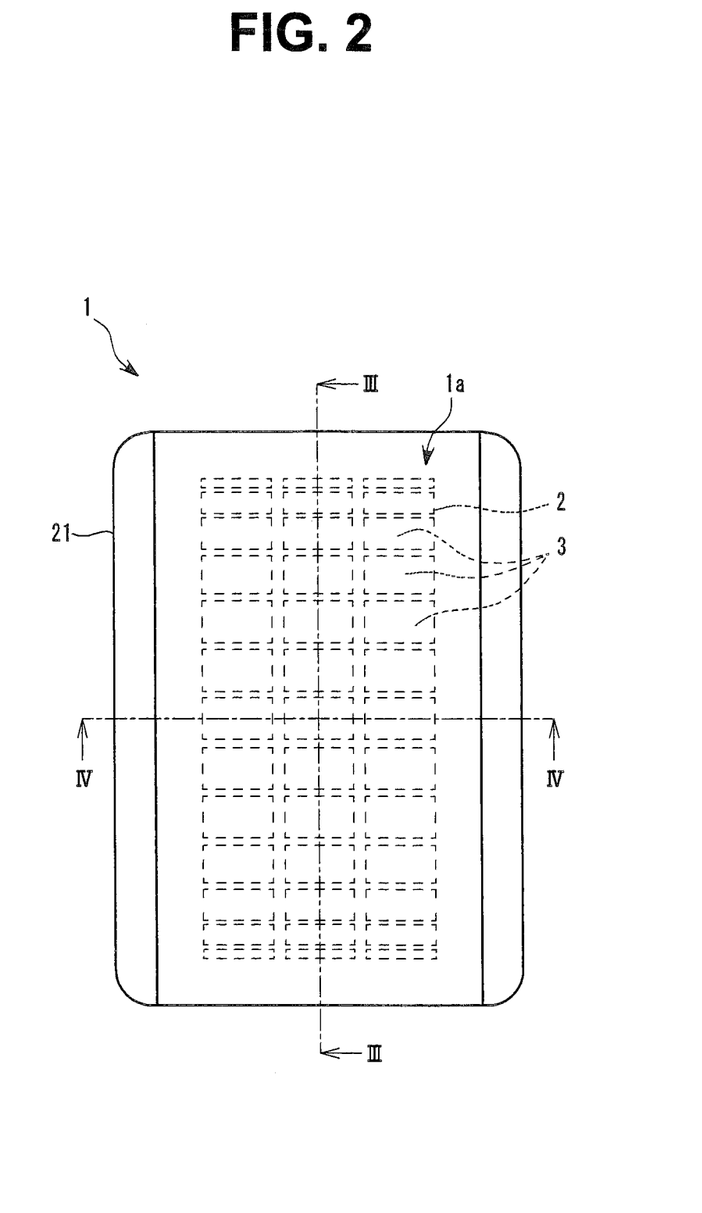
FIG. 2 is a diagram of the ultrasound transducer as viewed in a direction along a plane on which a scan using an ultrasound beam is performed.

An example of an embodiment of an ultrasound transducer according to the present invention will be described below. An ultrasound observation section 1 according to the present embodiment, which is illustrated in FIG. 1, includes an ultrasound transducer 1a that includes a piezoelectric element array 2 including a plurality of piezoelectric elements 3. The ultrasound transducer 1a is an electronic scanning ultrasound probe. FIG. 2 is a diagram of the ultrasound observation section 1 as viewed in a direction along a plane on which a scan using an ultrasound beam is performed by the ultrasound transducer 1a (referred to as a scan surface) (arrow A in FIG. 1).

Note that the count and the arrangement of the plurality of piezoelectric elements 3 included in the piezoelectric element array 2 are not specifically limited, and one-dimensional array (1D array) in which the plurality of piezoelectric elements 3 are arranged in a row, or a two-dimensional array (2D array) in which the plurality of piezoelectric elements 3 are arranged in a matrix may be employed.

Also, as forms of a piezoelectric element array including a plurality of piezoelectric elements arranged in a matrix, a configuration, generally called "1.25D array", that allows a width of an ultrasound beam to be varied, and a configuration, generally called "1.5D array", that allows a width and a focal length of an ultrasound beam to be varied are known. The piezoelectric element array 2 may employ such form called "1.25D array" or "1.5D array".

Also, where the piezoelectric element array 2 is a one-dimensional array, a form in which the plurality of piezoelectric elements 3 are arranged along a straight line or a form in which the plurality of piezoelectric elements 3 are arranged along a curved line may be employed. Also, where the piezoelectric element array 2 has a form in which a plurality of piezoelectric elements are arranged in a matrix like, for example, a 1.25D array, a 1.5D array or a 2D array, a form in which the plurality of piezoelectric elements 3 are arranged along one or a plurality of planes or a form in which the plurality of piezoelectric elements 3 are arranged along one or a plurality of curved surfaces may be employed.

In the present embodiment, as an example, the piezoelectric element array 2 included in the ultrasound transducer 1a has a form of a 1.25D array in which the plurality of piezoelectric elements 3 are arranged in a matrix on a substantially cylindrical plane. The piezoelectric element array 2 is configured so that a circumferential direction of the substantially cylindrical plane corresponds to a scan direction, and an ultrasound beam scan can be performed in a substantially fan-like form. The ultrasound observation section 1 including the piezoelectric element array 2 having such form is generally called "convex type".

Although described in detail later, the ultrasound transducer 1a is housed in a housing section 21. The housing section 21 is configured to hold the ultrasound transducer 1a with an ultrasound transmission/reception surface thereof exposed.

The ultrasound observation section 1 receives a signal sent from an ultrasound observation apparatus 22 via a connection portion 20 and generates ultrasound. Also, the ultrasound observation section transmits a received ultrasound signal to the ultrasound observation apparatus 22 via the connection portion 20, whereby an ultrasound image is obtained. In the present embodiment illustrated in FIG. 1, as an example, the connection portion 20 includes an electrical cable 20a extending from the ultrasound observation section 1, and a connector 20b provided at an end portion of the electrical cable 20a, the connector 20b being configured to be connectable to the ultrasound observation apparatus 22. The electrical cable 20a is electrically connected to the plurality of piezoelectric elements 3 via a later-described configuration.

Note that the form of the connection portion 20 is not limited to that of the present embodiment, and for example, a form in which the connector 20b is provided at the ultrasound observation section 1 with no electrical cable provided may be employed.

Figure 3:
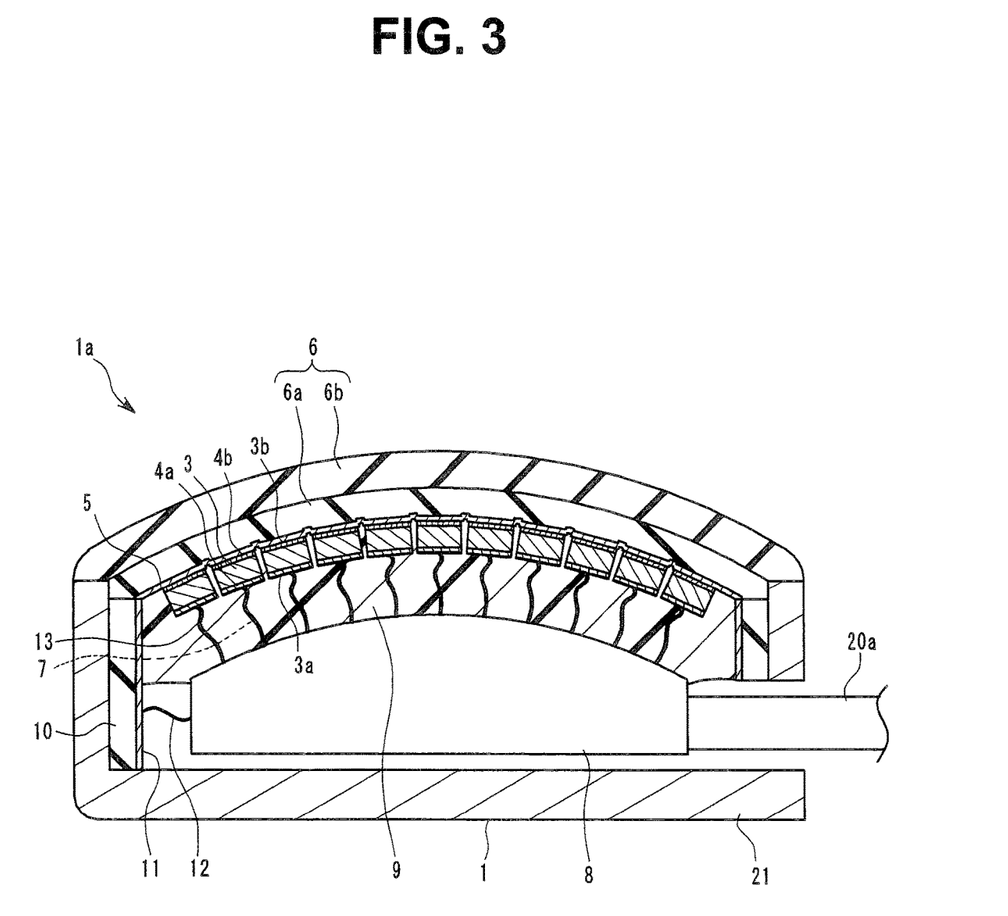
FIG. 3 is a cross-sectional view along III-III in FIG. 2, which is a cross sectional view of the ultrasound transducer cut along a plane parallel to a scan surface.
Figure 4:
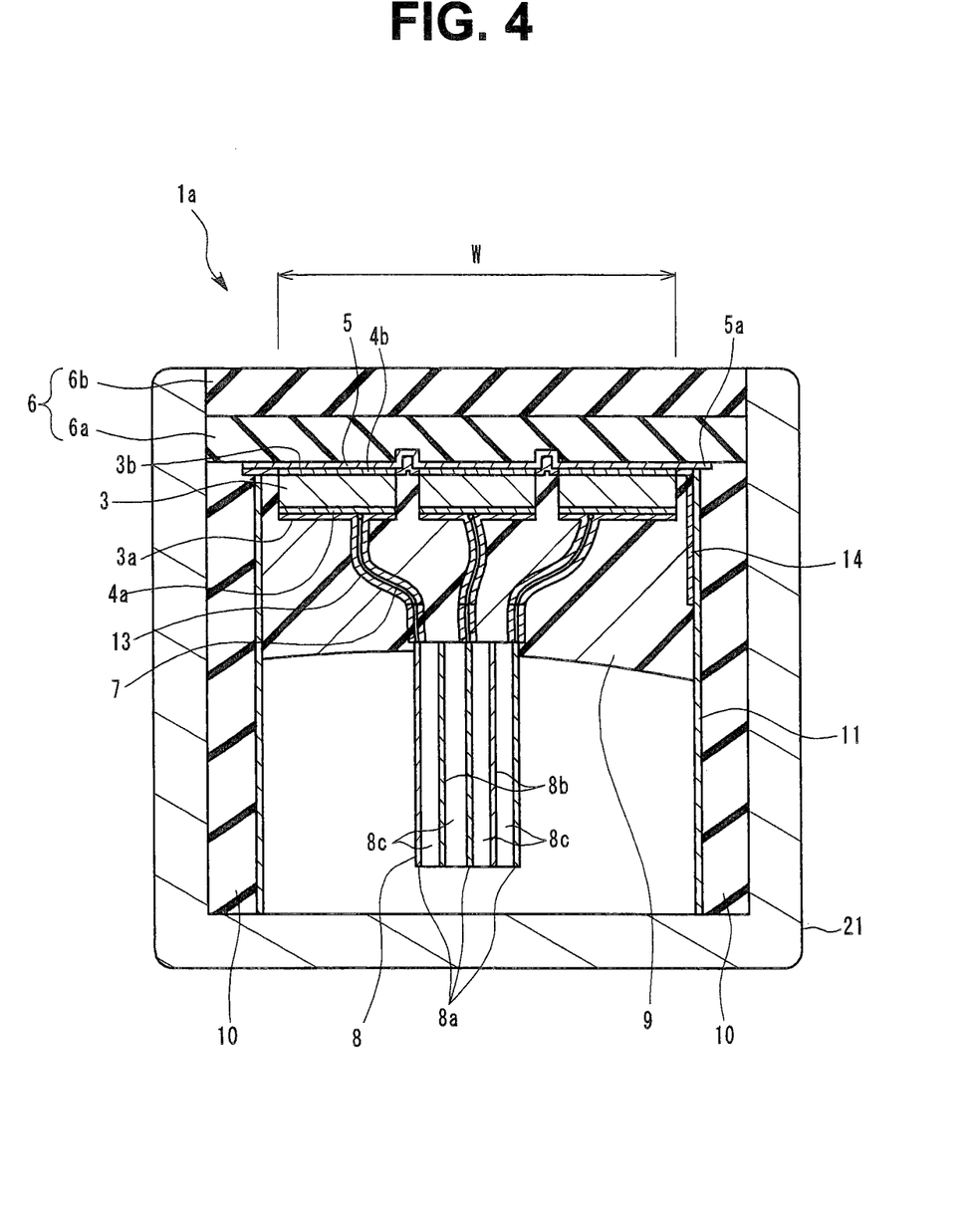
FIG. 4 is a cross-sectional view along IV-IV in FIG. 2, which is a cross-sectional view of the ultrasound transducer cut along a plane perpendicular to the scan surface.
Figure 5:
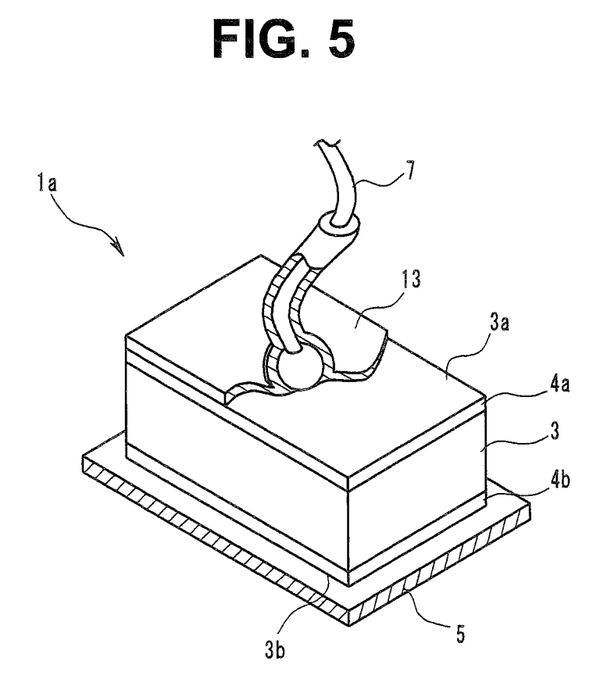
FIG. 5 is an enlarged perspective view of a single piezoelectric element.

A configuration of the ultrasound observation section 1 and a configuration of the ultrasound transducer 1a included in the ultrasound observation section 1 will be described in detail below. FIG. 3 is a cross-sectional view of the ultrasound observation section 1 cut along a plane parallel to a scan surface. FIG. 4 is a cross-sectional view of the ultrasound observation section 1 cut along a plane perpendicular to the scan surface. FIG. 5 is an enlarged perspective view of a single unit of a piezoelectric element 3 and a wire 7 included in the ultrasound transducer 1a.

Each of the piezoelectric elements 3 includes, for example, a PMN-PT single crystal, a PMN-PZT single crystal, a PZN-PT single crystal, a PIN-PZN-PT single crystal or a relaxer material.

The PMN-PT is an abbreviation of a lead magnesium niobate-lead titanate solid solution. The PMN-PZT single crystal is an abbreviation of a lead magnesium niobate-lead zirconate titanate solid solution.

The PZN-PT single crystal is an abbreviation of a lead zinc niobate-lead titanate solid solution.

The PIN-PZN-PT single crystal is an abbreviation of a lead indium niobate-lead zinc niobate-lead titanate solid solution.

The relaxer material is a general term of a three-component piezoelectric material formed by adding lead complex perovskite, which is a relaxer material, to lead zirconate titanate (PZT) for an increase in piezoelectric constant and/or permittivity. The lead complex perovskite is a material expressed by Pb(B1, B2)O3 in which B1 is any of magnesium, zinc, indium and scandium and B2 is any of niobium, tantalum and tungsten.

These materials provide an excellent piezoelectric effect. Thus, a value of electrical impedance can be made low even though the piezoelectric elements are downsized, which is favorable from the viewpoint of impedance matching between piezoelectric elements and wirings.

Each piezoelectric element 3 includes a first electrode 4a and a second electrode 4b, which form a pair of conductive layers. The first electrode 4a and the second electrode 4b are formed on principal surfaces of the piezoelectric element 3 that face in respective directions opposite to each other. Each of the first electrode 4a and the second electrode 4b includes a material having conductivity, for example, a metal thin film. In the below, the surface of each piezoelectric element 3 on which the first electrode 4a is formed is referred to as first face 3a, and the surface of each piezoelectric element 3 on which the second electrode 4b is formed is referred to as second face 3b.

The first electrode 4a, which is a conductive layer, is a signal electrode for input/output of a voltage signal from the respective piezoelectric element 3. Also, the second electrode 4b is a ground electrode having a ground potential. All the second electrodes 4b provided in the respective piezoelectric elements 3 are electrically connected to the same second conductive layer 5. The second conductive layer 5 is a ground electrode having a ground potential. Note that the second conductive layer 5 may be divided into a plurality of parts.

A distal end portion of a wire 7, which includes a conductive material, is bonded to each of the first electrodes 4a via a configuration that will described in detail later. The plurality of wires 7 extend from one or a plurality of circuit boards 8 toward the respective piezoelectric elements 3. The wires 7 are made of, for example, a metal such as gold or copper. On the circuit board 8, an electrical circuit that electrically connects the electrical cable 20a and the respective wires 7 is formed.

The circuit board 8 is a printed circuit board including one or a plurality of conductive layers. The circuit board 8 may be what is called a rigid circuit board including a base material including an electrical insulation material has a predetermined rigidness or what is called a flexible circuit board including a soft and flexible base material.

The wires 7 are provided between the first electrodes 4a and the circuit board 8, in a sagged state in which no tension is applied to the wires 7. Supposing that the wires 7 are in a tensioned state, the tension of the wires 7 is applied to the piezoelectric elements 3, which may hinder oscillation of the piezoelectric elements 3. As a result of bringing the wires 7 into a sagged state, an impact of tension of the wire 7 on oscillation of the piezoelectric elements 3 can be prevented or reduced.

Note that a cross-sectional shape of the wires 7 is not specifically limited, and may be a round shape, a rectangular shape or a flat shape. Also, the wires 7 may have a form of what is called a flying lead in which a part of the conductive layer(s) forming the electrical circuit of the circuit board 8 extends from an outer edge of the circuit board 8. In the present embodiment, as an example, for the wires 7, ones having a flat cross-sectional shape having a width of approximately 50 to 75 μm and a thickness of approximately 25 μm are used.

Also, as illustrated in FIGS. 3 and 4, a backing material 9 is disposed on surfaces of the first electrodes 4a on the side opposite to the piezoelectric element 3 side. The backing material 9 is a synthetic resin cured after being charged to the inner side of the piezoelectric elements 3 in the ultrasound observation section 1, and is provided to attenuate ultrasound from the piezoelectric elements 3 toward the inner side of the ultrasound observation section 1. The backing material 9 includes, for example, an epoxy resin with a filler such as alumina or zirconia dispersed therein.

Peripheries of the backing material 9 and the circuit board 8 are surrounded by side wall portions 10. A third conductive layer 11 is provided on an inner face of each side wall portion 10. The third conductive layer 11 includes a material having conductivity, and is, for example, a metal thin film.

The third conductive layer 11 is electrically connected to the circuit board 8 via a ground wire 12. On the circuit board 8, an electrical circuit having a ground potential is formed, and the ground wire 12 is connected to the electrical circuit having a ground potential. The third conductive layer 11 is configured to act as an electromagnetic shield.

Also, the second conductive layer 5 is electrically connected to the third conductive layer 11 via a later-described configuration. In other words, the second conductive layer 5 is electrically connected to the electrical circuit of the circuit board 8, the electrical circuit having a ground potential, via the third conductive layers 11 and the ground wires 12.

A surface of the second conductive layer 5 on the side opposite to the piezoelectric elements 3, an acoustic matching layer 6 is disposed. The acoustic matching layer 6 is provided to perform acoustic impedance matching between the piezoelectric elements 3 and an object or subject. In the present embodiment, as an example, the acoustic matching layer 6 is configured by depositing a first acoustic matching layer 6a and a second acoustic matching layer 6b, which form a plurality of layers formed of different materials. The first acoustic matching layer 6a is disposed on the side close to the piezoelectric elements 3 relative to the second acoustic matching layer 6b. Note that the acoustic matching layer 6 may include a single layer or three or more layers. Also, although in the present embodiment, the acoustic matching layer 6 is exposed in an outer surface of the ultrasound observation section 1, an acoustic lens may be provided on the outer side of the acoustic matching layer 6.

For more details, in the present embodiment, as illustrated in FIGS. 3 and 4, the second conductive layer 5, which is a metal thin film, is formed on an inner face of the first acoustic matching layer 6a. The plurality of piezoelectric elements 3 are disposed in a predetermined arrangement on the second conductive layer 5. The piezoelectric elements 3 are disposed in such a manner that the second electrodes 4b formed on the respective second faces 3b are electrically connected to the second conductive layer 5. As illustrated in FIG. 4, in the present embodiment, three rows of piezoelectric elements 3 are arranged along a scan direction. For example, where the ultrasound observation section 1 is used for an endoscope, a width of the piezoelectric element array 2 in a direction perpendicular to the scan surface (width indicated by W in FIG. 4) is around 2 to 6 mm.

For the circuit board 8 in the present embodiment, a glass epoxy substrate including glass fiber and an epoxy resin is used as an electrical insulating base material 8c. The circuit board 8 includes signal circuit layers 8a, which are conductive layers each forming a pattern of wirings electrically connected to the first electrodes 4a of the corresponding piezoelectric elements 3, and ground layers 8b, which are conductive layers that each have a ground potential and are each formed on an entire surface of the circuit board 8.

In the present embodiment, the circuit board 8 includes five conductive layers consisting of three signal circuit layer 8a and two ground layer 8b disposed among the three signal circuit layers 8a. Electrical insulating base materials 8c are interposed among the five conductive layers. Interposition of the ground layers 8b, which are each in the form of what is called a solid electrode, among the signal circuit layers 8a enables prevention of crosstalk among the plurality of signal circuit layers 8a. Note that the circuit board 8 may be divided into a plurality of parts in a thickness direction and a plane direction.

The circuit board 8 is disposed in such a manner that the thickness direction is substantially perpendicular to the scan surface of the ultrasound observation section 1 on the inner side relative to the first electrode 4a. In other words, the three signal circuit layers 8a are disposed so as to extend along the three rows of the piezoelectric elements 3. A positional relationship between the piezoelectric elements 3 and the circuit board 8 is fixed by the backing material 9.

The three signal circuit layers 8a have respective wiring patterns corresponding to the three rows of piezoelectric elements 3, respectively. In other words, in FIG. 4, the center signal circuit layer 8a provides an electrical circuit electrically connected to the first electrodes 4a of the piezoelectric elements 3 included in the center row, the signal circuit layer 8a on the right side in the Figure provides an electrical circuit electrically connected to the first electrodes 4a of the piezoelectric elements 3 included in the right row in the Figure, and the signal circuit layer 8a on the left side in the Figure provides an electrical circuit electrically connected to the first electrodes 4a of the piezoelectric elements 3 included in the left row in Figure.

The wiring patterns formed by the signal circuit layers 8a of the circuit board 8 and the first electrodes 4a of the piezoelectric elements 3 are electrically connected by the wires 7. Here, a form of the electrical connection between the wiring patterns of the circuit board 8 and proximal ends of the wires 7 is not specifically limited. For example, a form in which the wiring patterns of the circuit board 8 and the proximal ends of the wires 7 are connected by means of, e.g., soldering or a conductive adhesive, or a form in which the wiring patterns of the circuit board 8 and the proximal ends of the wires 7 are connected by means of a bonding method known as what is called a wire bonding method may be employed. Also, as described above, the wires 7 may have a form of flying leads that are formed by making the signal circuit layers 8a of the circuit board 8 extend outward and are integrated with the wiring patterns at the proximal ends thereof.

In the other hand, as illustrated in FIG. 5, the distal ends of the wires 7 and the first electrodes 4a of the piezoelectric elements 3 that are in contact with each other are bonded by at least surfaces of the distal end portions of the wires 7 and the first electrodes 4a being coated with a metal film 13 having a predetermined thickness.

The metal film 13 is formed by an electroplating method. Although described in detail later, the metal film 13 is formed by immersing at least the distal end portions of the wires 7 and the first electrodes 4a that are in contact with each other in an electrolyte solution (plating solution) and making current flow in the wires 7 so that the wires 7 and the first electrodes 4a are plated.

Therefore, as illustrated in FIG. 5, the distal end sides of the wires 7 are coated in a cylindrical shape by the metal film 13 having a uniform thickness, and the first electrodes 4a are also coated in a uniform thickness that is equal to the thickness of the coating of the wire 7 by the metal film 13.

This is specific to an electroplating method, and with a conventional method using soldering, wires cannot be coated by a metal film having a uniform thickness, and neither a chemical vapor deposition (CVD) method nor a physical vapor deposition (PVD) method can also provide such coating. Furthermore, use of an electroplating method prevents thermal load from being imposed on the piezoelectric elements, whereby depolarization of the piezoelectric elements is suppressed, enabling prevention of piezoelectric effect decrease or elimination.

There are no specific limitations on the thickness and the material of the metal film 13 and the detailed method of electroplating as long as they provide electrical connection between the distal ends of the wires 7 and the first electrodes 4a of the piezoelectric elements 3 by means of the coating with the metal film 13.

For example, when the metal film 13 is formed, use of a pulse plating method in which current is made to flow intermittently makes the metal film 13 dense and enhances the reliability of bonding provided by the metal film 13 and thus is preferable.

Also, for example, if the metal film 13 is formed by nickel sulfamate plating or copper pyrophosphate plating, inner stress in the metal film 13 can be reduced to be lower than that provided by any other nickel plating, enabling the metal film 13 to be relatively thick. Also, in order to reduce inner stress in the metal film 13, a stress reliever may be used in the electroplating.

For example, an upper limit of the thickness of the metal film 13 is determined as follows, according to physical properties of the material forming the metal film 13 and a wavelength of ultrasound to be transmitted/received by the ultrasound observation section 1. In the present embodiment, where a wavelength, in the material forming the metal film 13, of ultrasound having a highest frequency from among ultrasounds to be transmitted/received by the ultrasound observation section 1 is $\lambda$, an upper limit tmax of the thickness of the metal film 13 is preferably $\lambda/10$ or less, more preferably, $\lambda/20$ or less.

For example, where the metal film 13 is of nickel, a longitudinal sound velocity C in nickel is approximately 6000 m/s. Here, where the upper limit of the frequency of ultrasound to be transmitted/received by the ultrasound observation section 1 is 15 MHz, the wavelength $\lambda$ of the ultrasound in nickel is approximately 400 µm. Therefore, the upper limit tmax of the thickness of the metal film 13 where the metal film 13 is of nickel is preferably 40 µm, more preferably 20 µm.

Also, for example, where the metal film 13 is of copper, a longitudinal sound velocity C in copper is approximately 5000 m/s. Here, where the upper limit of the frequency of ultrasound to be transmitted/received by the ultrasound observation section 1 is 15 MHz, the wavelength 2 of the ultrasound in copper is approximately 333 µm. Therefore, the upper limit tmax of the thickness of the metal film 13 where the metal film 13 is of copper is preferably 33 µm, more preferably 16 µm.

In the present embodiment, the thickness of the metal film 13 is, for example, no less than 0.1 µm and no more than 15 µm, preferably approximately no less than 0.5 µm and no more than 5 µm in consideration of a balance between a bonding strength and a current capacity, and an effect of existence of the metal film 13 on acoustic properties of the piezoelectric element 3.

Also, as described above, it is preferable that the wires 7 be bonded to the first electrodes 4a in a sagged state in which no tension is applied to the wires 7. Furthermore, it is preferable that the wires 7 be handled so as to include no parts that are parallel to the first faces 3a of the piezoelectric elements 3. This is intended to prevent ultrasound transmitted from the first faces 3a of the piezoelectric elements 3 from being reflected by the wires 7 and returned to the piezoelectric elements 3.

Also, in the present embodiment, as illustrated in FIG. 5, at a stage before bonding between the wires 7 and the first electrodes 4a, the distal ends of the wires 7 are melted to have a substantially spherical shape. As a result of the distal ends of the wires 7 having a substantially spherical shape, the area of contact between the distal end of each wire 7 and the corresponding first electrode 4a can be kept substantially constant regardless of the angle of the distal end of the wire 7 relative to the first electrode 4a, whereby the electrical connection between the distal end of the wire 7 and the first electrode 4a is stabilized.

As in the present embodiment, for example, depending on the type of the metal used, bonding the wires 7 and the first electrodes 4a by means of the metal film 13 enables provision of a high chemical resistance compared to bonding using a conductive adhesive or an anisotropic conductive sheet.

Also, in the present embodiment, for all the piezoelectric elements 3 included in the piezoelectric element array 2, the wires 7 and the first electrodes 4a are bonded by a homogeneous metal film 13 formed by an electroplating method. Thus, the bonding between the wires 7 and the first electrodes 4a is homogeneous in the entire piezoelectric element array 2, enabling reduction in variation of electrical resistance in bonding parts, which occurs when a conductive resin is used. Therefore, transmission and reception characteristics of the ultrasound transducer 1a can be stabilized.

On the inner face of the first acoustic matching layer 6a, the side wall portions 10 are provided in a standing manner so as to surround the piezoelectric element array 2, the circuit board 8 and the wires 7. On the inner face of each side wall portion 10, the third conductive layer 11 is formed.

The second conductive layer 5 formed on the inner face of the first acoustic matching layer 6a includes extension portions 5a, each extending to a region in which the extension portion 5a is in contact with a part of the corresponding third conductive layer 11, and thus the third conductive layers 11 and the second conductive layer 5 are partly in contact with each other.

Then, a metal film 14 is formed on an inner face of each part in which the third conductive layer 11 and the second conductive layer 5 are in contact with each other, and the metal films 14 provide electrical connection between the third conductive layers 11 and the second conductive layer 5.

The metal films 14 are ones formed by an electroplating process that is the same as that for the above-described metal film 13 bonding the distal ends of the wires 7 and the first electrodes 4a, include a material that is the same as that of the metal film 13, and have a thickness that is substantially equal to that of the metal film 13.

Next, a method for manufacturing the ultrasound transducer 1a having the above-described configuration will be described.

Figure 6:
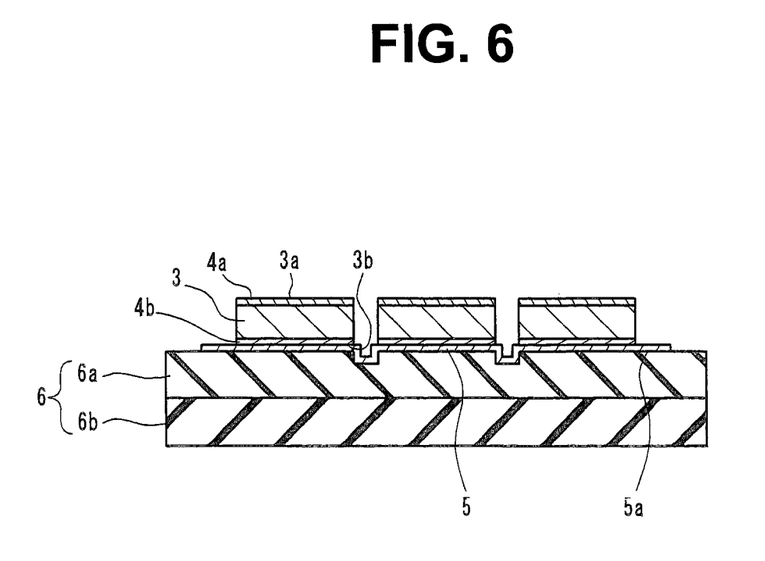
FIG. 6 is a diagram for describing an ultrasound transducer manufacturing method.

First, as illustrated in FIG. 6, a second conductive layer 5 is formed on a predetermined region or an entirety of an inner face of a first acoustic matching layer 6a. Then, a plurality of piezoelectric elements 3 are disposed on an inner face of the second conductive layer 5. Here, a second electrode 4b formed on a second face 3b of each piezoelectric element 3 is made to abut on an inner face of the second conductive layer 5, whereby the second electrode 4b and the inner face are brought into electrical contact with each other. Consequently, a first electrode 4a formed on a first face 3a of each piezoelectric element 3 is in an exposed state.

Figure 7:
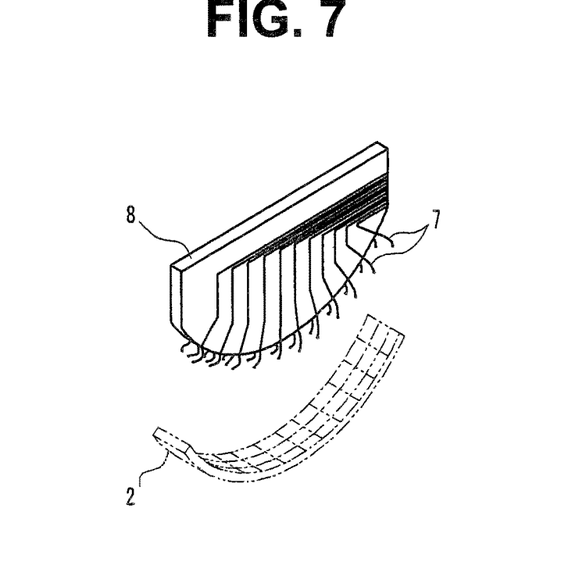
FIG. 7 is a diagram for describing the ultrasound transducer manufacturing method.

Also, as illustrated in FIG. 7, a plurality of wires 7 extending from a circuit board 8 are shaped so as to be in contact with the respective first electrodes 4a of the plurality of piezoelectric elements 3 forming a piezoelectric element array 2.

Figure 8:
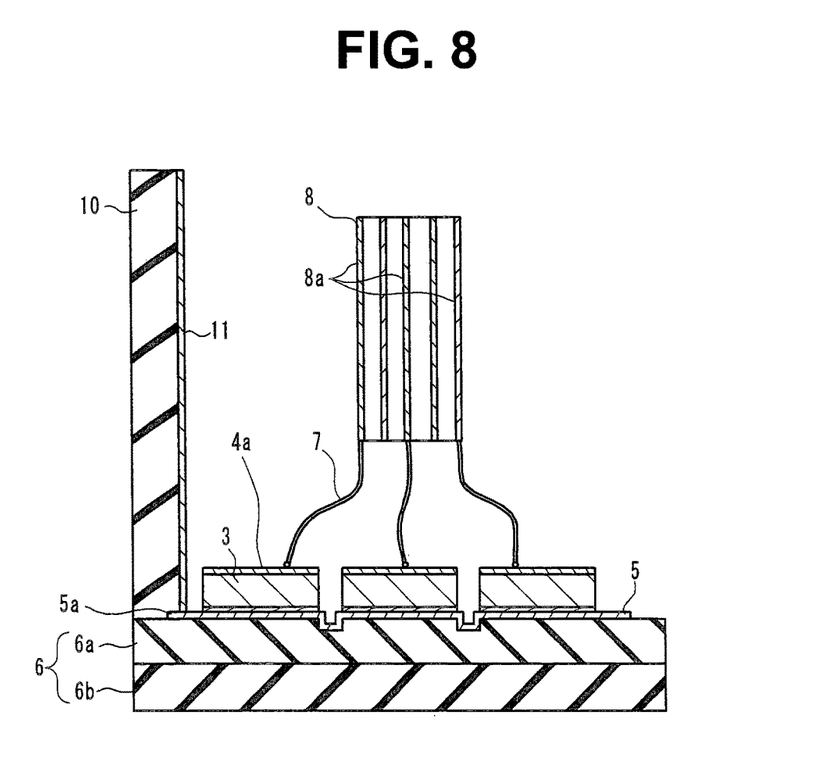
FIG. 8 is a diagram for describing the ultrasound transducer manufacturing method.

Then, as illustrated in FIG. 8, relative positions of the first acoustic matching layer 6a and the circuit board 8 are fixed using a non-illustrated jig so that distal ends of all wires 7 are in contact with the corresponding first electrodes 4a. Also, in this process, side wall portions 10 are fixed by, e.g., an adhesive so that third conductive layers 11 and extension portions 5a of the second conductive layer 5 are in electrical contact with each other.

Figure 9:
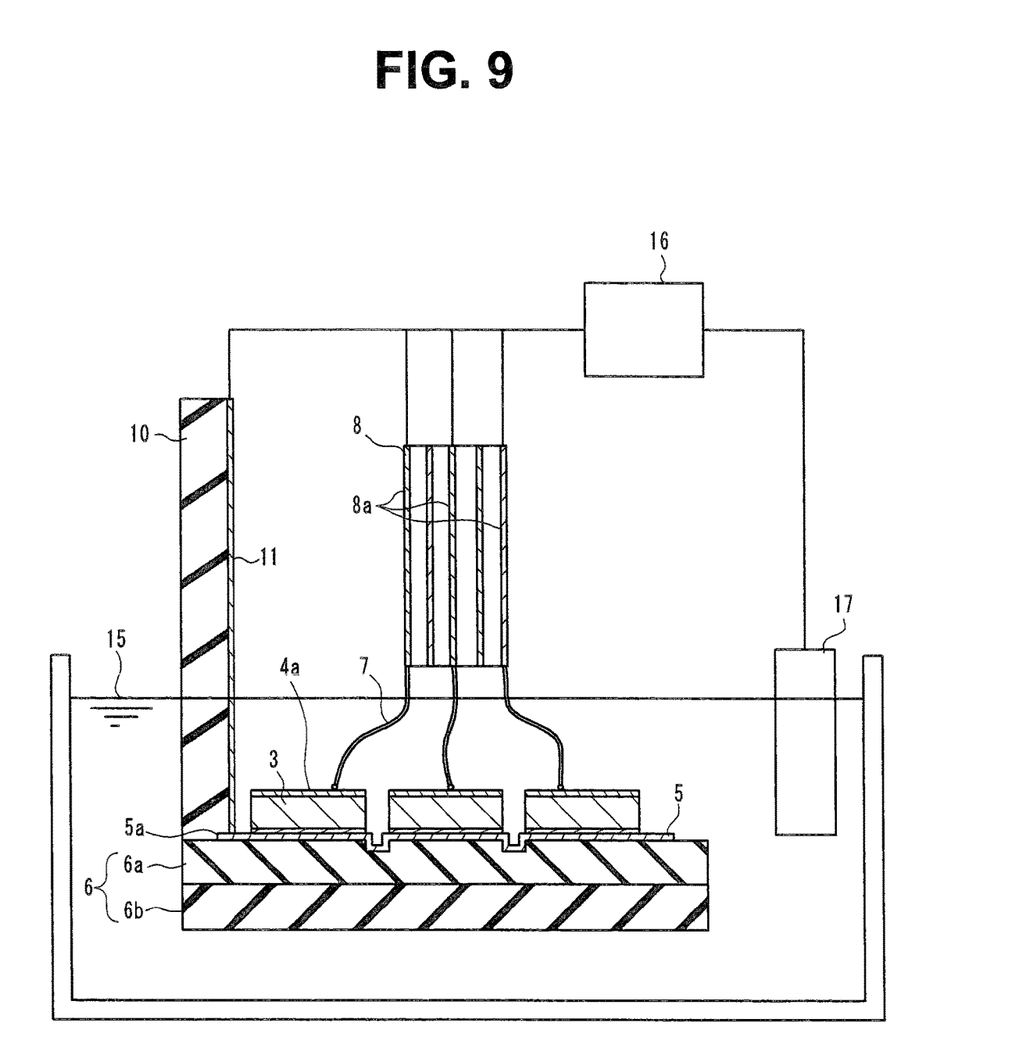
FIG. 9 is a diagram for describing an electroplating process in the ultrasound transducer manufacturing method.

Next, as illustrated in FIG. 9, parts of contact between the distal ends of the wires 7 and the first electrodes 4a are immersed in an electrolyte solution 15. Also, parts of contact between the third conductive layers 11 and the second conductive layer 5 are also immersed in the electrolyte solution. Then, an electroplating process in which current is made to flow between all the wires 7 and the third conductive layers 11, and an electrode 17 immersed in the electrolyte solution 15 under a predetermined condition using a power supply apparatus 16 is performed. In the present embodiment, a nickel sulfamate bath is used as an electroplating method.

In the electroplating process, a plating film of nickel is formed on surfaces of the wires 7 and surfaces of the first electrodes 4a that are in contact with the distal ends of the wires 7, which are immersed in the electrolyte solution 15. Also, a plating film of nickel is formed on surfaces of parts of the third conductive layers 11 and the second conductive layer 5 immersed in the electrolyte solution 15.

Figure 10:
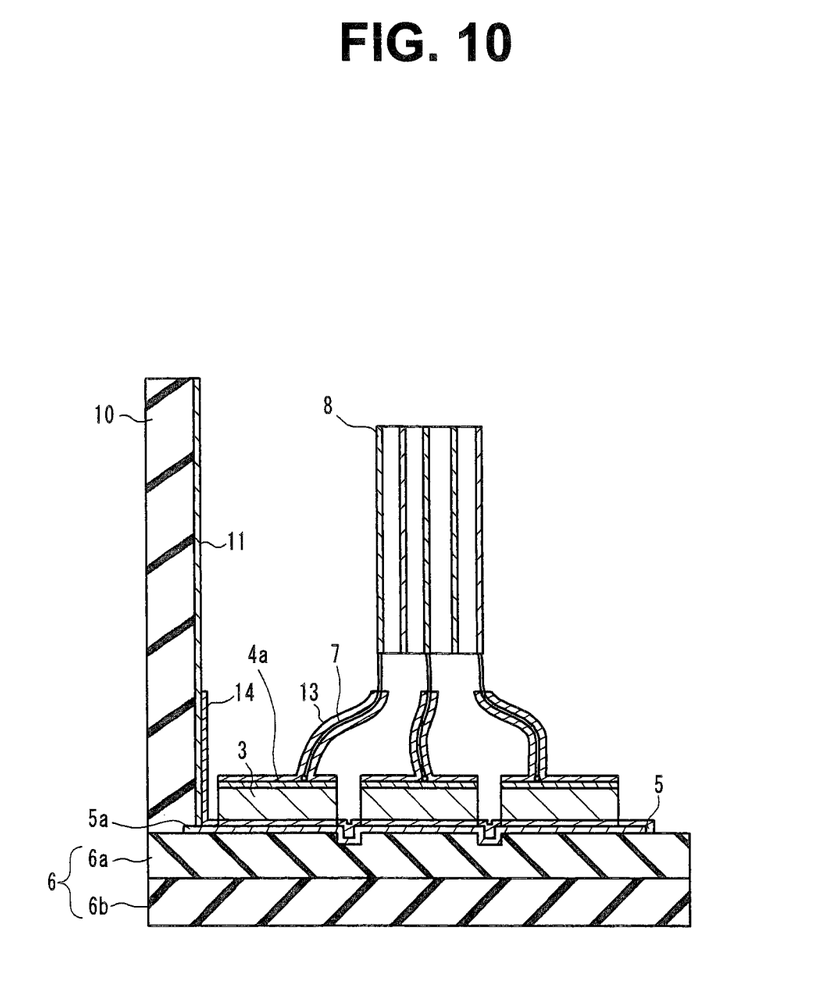
FIG. 10 is a diagram for describing the ultrasound transducer manufacturing method.

Then, as illustrated in FIG. 10, after the electroplating process, the distal end portions of the wires 7 and the first electrodes 4a are coated and bonded by the metal film 13 of nickel having a predetermined thickness. Also, after the electroplating process, the parts of contact between the third conductive layers 11 and the second conductive layer 5 are bonded by the metal film 14 of nickel having the predetermined thickness. Then, although not illustrated, the third conductive layers 11 and ground layers 8b are electrically connected by ground wires 12.

Figure 11:
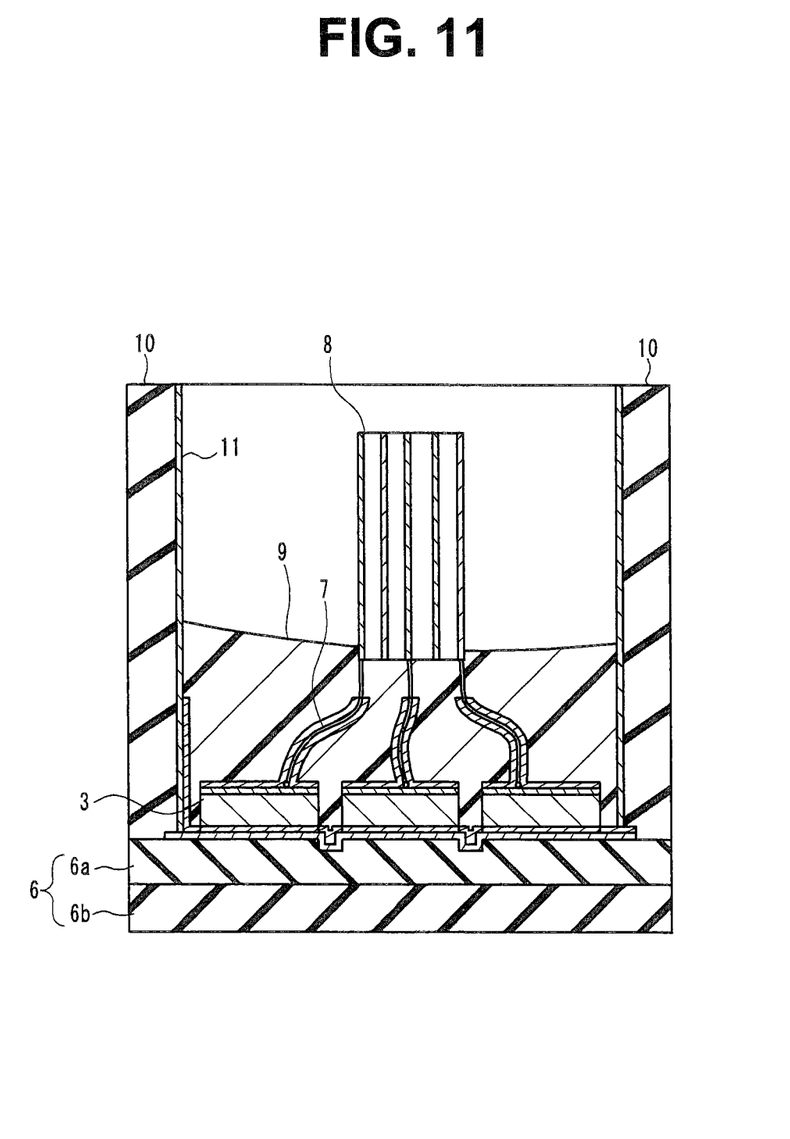
FIG. 11 is a diagram for describing the ultrasound transducer manufacturing method.

Next, as illustrated in FIG. 11, the entire side wall portions 10 are fixed to a first acoustic matching layer 6a, and a backing material 9 is charged and cured in a space surrounded by the side wall portions 10. As a result of the backing material 9 being cured, the circuit board 8 is fixed to the first acoustic matching layer 6a.

Note that a process of coating surfaces of the metal films 13 and 14 with an electrical insulating material may be added between the formation of the metal films 13 and 14 by the electroplating process and the charging of the backing material 9. The coating with the electrical insulating material can be formed by, for example, an electrodeposition method. As descried above, peripheries of the wires 7 are coated by an electrical insulating material, enabling prevention of deformation of a wire 7 and short-circuit between the wire 7 and another wire 7 when the backing material 9 is charged.

Figure 12:
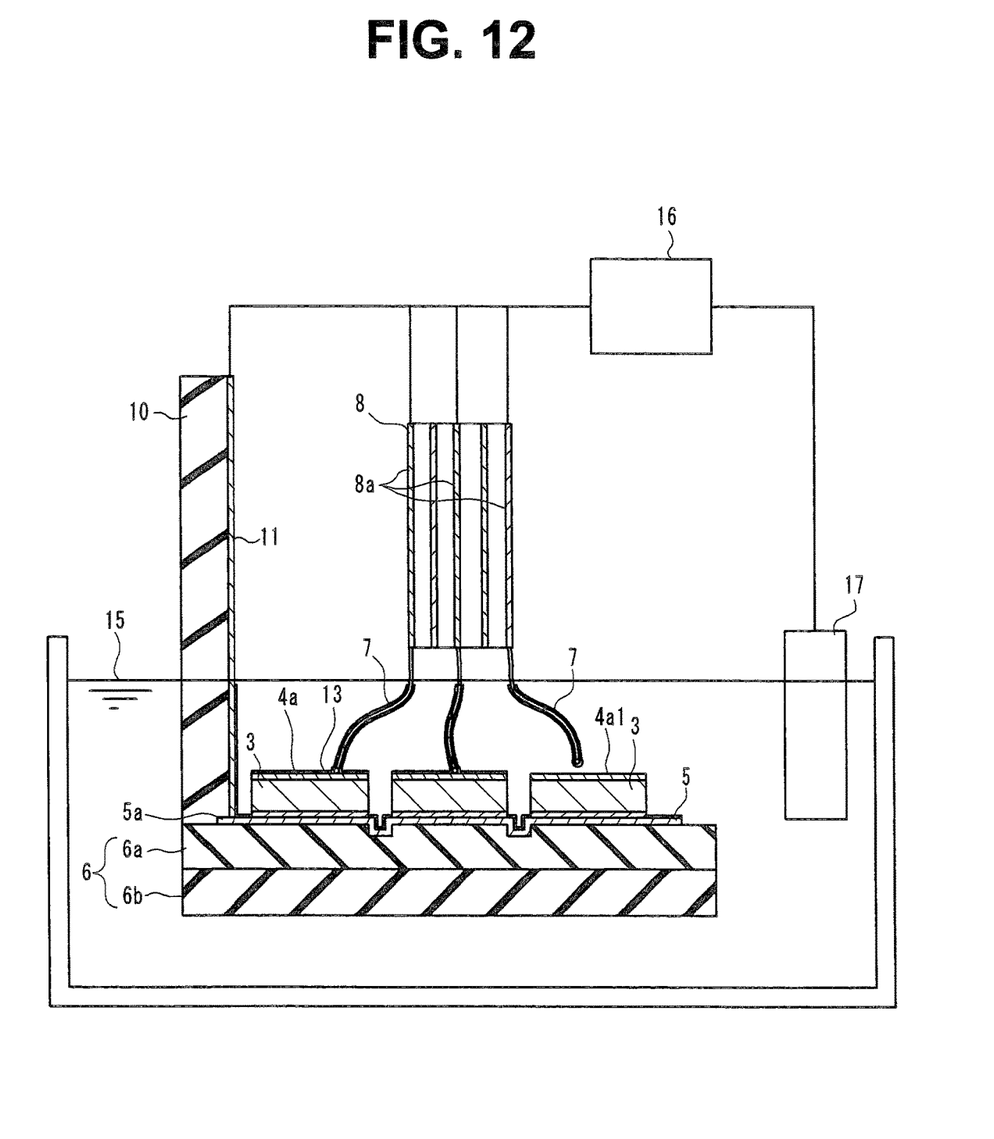
FIG. 12 is a diagram for describing an effect of the ultrasound transducer manufacturing method.

In the manufacturing method described above, for example, as illustrated in FIG. 12, where the electroplating process is started in a state in which the distal end of a wire 7 is not in contact with the corresponding first electrode 4a, no metal film 13 is formed on the first electrode 4a1 (the right first electrode 4a in FIG. 12) that is not in contact with the wire 7. Thus, in the present embodiment, whether or not the respective wires 7 are in contact with the corresponding first electrodes 4a can visually be checked easily and reliably during the electroplating process. If such check is made at an early stage of the electroplating process and the work for correcting the shape of a wire 7 for a first electrode 4a1 with no metal film 13 formed thereon is performed, bonding between all the wires 7 and the first electrodes 4a can be ensured.

As described above, the ultrasound observation section 1 according to the present embodiment includes: the plurality of piezoelectric elements 3, the first electrode 4a formed on one surface of each piezoelectric element 3, the conductive wire 7 including a distal end that is in contact with the first electrode 4a; and the metal film 13 formed by an electroplating method, the metal film 13 coating at least the distal end of the wire 7 in a uniform thickness along a shape of the wire 7 and further coating the first electrode 4a in a thickness that is equal to the thickness of the coating of the wire 7.

In the ultrasound observation section 1 according to the present embodiment, an electrical wiring connected to a first electrode 4a, which is an electrode of each piezoelectric element 3, is a thin wire 7, and the first electrodes 4a and the wires 7 are bonded by the metal film 13, which is a conductive thin film formed by an electroplating method.

Therefore, the first electrodes 4a and the wires 7 can be bonded without heating of the piezoelectric elements 3 to a temperature at which the piezoelectric elements 3 are depolarized, enabling provision of an ultrasound transducer with suppressed piezoelectric element depolarization during manufacture.

Furthermore, in the present embodiment, members that are in contact with the respective piezoelectric elements 3 for electrical wiring are the wires 7 and the metal film 13 only, which are light, and an effect of these members for wiring on oscillation of the piezoelectric elements 3 is very small. Therefore, the ultrasound observation section 1 according to the present embodiment enables use of fine piezoelectric elements 3 while deterioration in acoustic properties is suppressed. This contributes to, for example, enhancement in resolution and sensitivity of small-size ultrasound transducers that can be introduced into a living body such as a human body, such as ultrasound endoscopes.

Furthermore, in the present embodiment, for all the piezoelectric elements 3 included in the ultrasound transducer 1a, the wires 7 and the first electrodes 4a are bonded by a homogenous metal film 13 formed by one electroplating process. Therefore, the work for electrical wiring is considerably easy compared to, for example, cases where a wire is bonded to each piezoelectric element by means of soldering, and a piezoelectric element array 2 using finer piezoelectric elements 3 can be manufactured.

Also, in the present embodiment, it is preferable that each piezoelectric element 3 includes a PMN-PT single crystal, a PMN-PZT single crystal, a PZN-PT single crystal, a PIN-PZN-PT single crystal or another relaxer material. A piezoelectric element 3 including any of these materials has a low Curie point, and thus is depolarized when a heating process such as soldering is used, resulting decrease or elimination of the piezoelectric effect. In the present embodiment, the wires 7 and the first electrodes 4a can be bonded by an electroplating method without heating, enabling use of any of these materials having large relative permittivity. As a result of the piezoelectric elements 3 being formed by a material having large relative permittivity, as described above, a value of electrical impedance can be made low even if the piezoelectric elements 3 are miniaturized.

Note that the present invention is not limited to the above-described embodiment, and arbitrary alterations can be made without departing from the spirit and idea of the invention that can be read from the claims and the entire description, and an ultrasound transducer and an ultrasound transducer manufacturing method with such change also fall within the technical scope of the present invention.

What is claimed is:

1. An ultrasound transducer comprising:
   at least one piezoelectric element;
   an electrode formed on a surface of the piezoelectric element;
   at least one conductive wire including a distal end that is in contact with the electrode;
   a metal film formed by an electroplating method, the metal film coating at least the distal end of the wire and the electrode that are in contact with each other such that no tension is applied to the wire, the metal film electrically connecting the electrode and the wire, an upper limit of a thickness of the metal film being not greater than one tenth a wavelength, in a material forming the metal film, of ultrasound having a highest frequency to be transmitted and received by the piezoelectric element; and
   a backing material charged in peripheries of the electrode and the metal film.

2. The ultrasound transducer according to claim 1, wherein the distal end of the wire has a spherical shape.

3. The ultrasound transducer according to claim 1, wherein the piezoelectric element includes a PMN-PT single crystal, a PMN-PZT single crystal, a PZN-PT single crystal, a PIN-PZN-PT single crystal or a relaxer material.

4. The ultrasound transducer according to claim 1, wherein the distal end contact with the electrode comprises a butt connection of the distal end against a surface of the electrode.

5. The ultrasound transducer according to claim 1, wherein
   the at least one piezoelectric element comprises a plurality of piezoelectric elements;
   the at least one conductive wire comprises a plurality of conductive wires comprising distal ends respectively in contact with a plurality of electrodes formed on the plurality of piezoelectric elements; and
   the metal film is formed by electroplating in which all of the electrodes and all of the distal ends of the wires are brought into contact with one another and immersed in a same plating solution.

6. The ultrasound transducer according to claim 1, wherein the wire is formed by extending a part of a conductive layer that forms an electrical circuit of a circuit board from an outer edge of the circuit board.

7. The ultrasound transducer according to claim 1, wherein a coating with an electrical insulating material that coats the metal film is formed between the metal film and the backing material.

8. An ultrasound transducer manufacturing method comprising:
   a first step of bringing a distal end of a conductive wire into contact with an electrode formed on a surface of a piezoelectric element such that no tension is applied to the wire;
   a second step of, with the distal end of the wire and the electrode in contact with each other, coating at least the distal end of the wire with a metal film formed by an electroplating method and further coating the electrode, and thereby electrically connecting the wire and the electrode, an upper limit of a thickness of the metal film being not greater than one tenth a wavelength, in a material forming the metal film, of ultrasound having a highest frequency to be transmitted and received by the piezoelectric element; and
   a third step of charging a backing material in peripheries of the electrode and the metal film.

9. The ultrasound transducer manufacturing method according to claim 8, wherein the first step comprises butting the distal end against a surface of the electrode.

10. The ultrasound transducer manufacturing method according to claim 8, wherein
    in the first step, distal ends of a plurality of conductive wires are respectively brought into contact with electrodes formed on surfaces of a plurality of piezoelectric elements, and
    in the second step, the metal film is formed by electroplating in which all of the electrodes and all of the distal ends of the wires are brought into contact with one another and immersed in a same plating solution.

11. The ultrasound transducer manufacturing method according to claim 8, further comprising forming a coating with an electrical insulating material that coats the metal film between the second and third steps.

* * * * *